(12) United States Patent
Ikeda (10) Patent No.: US 8,945,946 B2
(45) Date of Patent: Feb. 3, 2015

(54) SENSOR ELEMENT AND DETECTION METHOD OF MAGNETIC PARTICLES USING THIS ELEMENT, AND DETECTION METHOD OF TARGET SUBSTANCE

(75) Inventor: Takashi Ikeda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 344 days.

(21) Appl. No.: 11/727,666

(22) Filed: Mar. 28, 2007

(65) Prior Publication Data

US 2007/0231926 A1   Oct. 4, 2007

(30) Foreign Application Priority Data

Mar. 31, 2006  (JP) ................................. 2006-100560

(51) Int. Cl.
    *G01N 33/553*  (2006.01)
    *G01N 33/53*   (2006.01)
    *G01N 33/543*  (2006.01)
    *G01N 27/74*   (2006.01)

(52) U.S. Cl.
    CPC .......... *G01N 33/54326* (2013.01); *G01N 33/53* (2013.01); *G01N 27/745* (2013.01)
    USPC ....................... 436/526; 435/287.2

(58) Field of Classification Search
    None
    See application file for complete search history.

(56) References Cited

U.S. PATENT DOCUMENTS

| 6,046,585 A | 4/2000 | Simmonds |
| 2003/0231445 A1* | 12/2003 | Juds et al. ........................ 361/56 |
| 2005/0287681 A1 | 12/2005 | Nishiuma et al. ............. 436/524 |
| 2007/0237673 A1 | 10/2007 | Ikeda et al. ..................... 422/61 |

FOREIGN PATENT DOCUMENTS

CN   1279764 A   1/2001

OTHER PUBLICATIONS

Ferreira (2005) IEEE Transactions 41:4140-4142.*
Ferreira et al. [Ferreira et al., Detection of cystic fibrosis related DNA targets using AC field focusing of magnetic labels and spin-valve sensors, Oct. 2005, IEEE Transactions on Magnetics, 40(10): pp. 4140-44142].*
Hugo A. Ferreira, et al., "Detection of Cystic Fibrosis Related Dna Targets Using AC Field Focusing of Magnetic Labels and Spin-Valve Sensors", IEEE Transactions on Magnetics, vol. 41, No. 10, Oct. 2005, pp. 4140-4142.
D. L. Graham, et al., "Magnetic field-assisted DNA hybridisation and simultaneous detection using micron-sized spin-valve sensors and magnetic nanoparticles", Sensors and Actuators B, vol. 107, 2005, pp. 936-944.
Official Action dated Aug. 21, 2009 in Chinese Application No. 200700917330.

* cited by examiner

*Primary Examiner* — Chris L Chin
*Assistant Examiner* — Richard Moerschell
(74) *Attorney, Agent, or Firm* — Fitzpatrick, Cella, Harper and Scinto (57) ABSTRACT

A sensor device is configured by using a sensor element including functions as a magnetic field sensor and capable of generating the magnetic field for collecting magnetic particles on a sensor surface by the application of the current. As a result, a sensor device can be provided in which the magnetic particles serving as a label can be effectively collected on the sensor, and at the same time, the influence given to the sensor by the magnetic field for collecting the magnetic particles can be reduced.

5 Claims, 6 Drawing Sheets

SENSOR ELEMENT AND DETECTION METHOD OF MAGNETIC PARTICLES USING THIS ELEMENT, AND DETECTION METHOD OF TARGET SUBSTANCE

BACKGROUND OF THE INVENTION

1. Field of the Invention

The present invention relates to a sensor device for detecting magnetic particles contained in a specimen or a target substance contained in a specimen with the magnetic particles as a label and a detection method.

2. Description of the Related Art

As a quantitative immunoassay, RIA or IRMA (radio immunoassay or immunoradiometric assay) have been known since a long time ago. According to this method, a competitive antigen or antibody is labeled by a radioactive nuclide, and from a measurement result of specific activity, the antigen is quantitatively measured. That is, the target substance such as the antigen is labeled, and is indirectly measured. Since this method has a high sensibility, it has greatly contributed to clinical diagnosis, but because of a problem of safety of radioactive nuclide, it has a weak side that requires a dedicated facility and apparatus. Hence, as a more workable method, for example, a method of using a label such as fluorescent material, enzyme, electrochemical emission molecule, and magnetic particles has been proposed. When a fluorescent label, enzyme label, electrochemical emission label, and the like are used as a label, they are used for an optical measuring method, and by measuring absorption coefficient and transmittivity of a light or an emitted light amount, the detection of the target substance is performed. EIA (Enzyme Immunoassay) using enzyme for a label is a method in which an antigen-antibody reaction is acted, and after that, an enzyme labeled antibody is reacted, and a substrate for the enzyme is added so as to cause color formation, and depending on its absorbance, colorimetry is carried out. Further, research papers on a biosensor for indirectly detecting biomolecule by a magnetic sensor element with the magnetic particles as a label have been issued by several research organizations.

Figure 7:
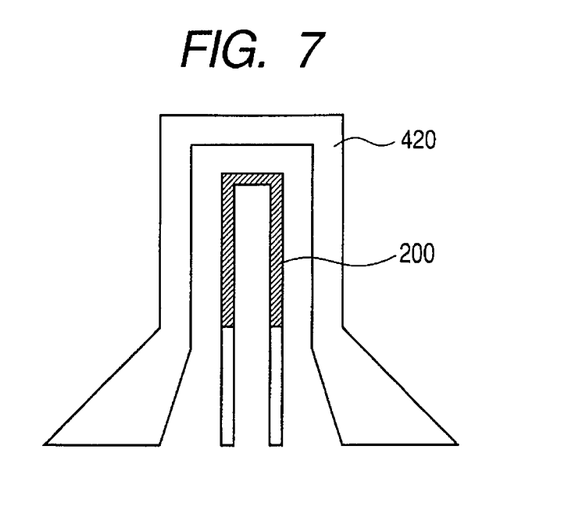
FIG. 7 is a conceptual illustration to describe the disposition of a magnetic sensor and a magnetic generating wiring disclosed in Document 1.

The magnetic particles as a label need to be selectively immobilized on the target substance, and to obtain high detecting sensitivity and few variations in measurement value, it was necessary that a large number of labels are reacted enough time. Hence, when the magnetic particles are used for a label, as illustrated in FIG. 7, an idea is proposed, in which a wiring 420 for generating a magnetic field is disposed around a magnetic sensor 200, and by letting flow the current into this wiring 420, the magnetic field is generated to attract the magnetic particles, and contact probability with the magnetic particle and the target substance is increased so that the reaction is effectively carried out, thereby solving the above described problem. (Hugo A. Ferreira et al., IEEE Trans. Magn. 41, 4140 (2005) (hereinafter, referred to as Document 1)).

The technique disclosed in Document 1 is useful from the viewpoint of collecting the magnetic particles from a wider range. However, when attention is paid to a narrower range, it is recognized that the place in which the magnetic particles tend to come together is on the wiring to generate the magnetic field, and this is not enough for the purpose of collecting the magnetic particles on the sensor. Further, since a large magnetic field needs to be generated in order to collect the magnetic particles, there is a problem, for example, that it affects the magnetic sensor comprising a magnetic substance such as a magneto-resistive effect film.

A constitution as an improvement of the above wherein a magnetic particles collection efficiency was increased has been proposed in D. L. Graham et al., Sensors and Actuators B 107, 936 (2005). In the constitution, the magnetic particles is collected on a wiring provided in the vicinity of a giant magneto-resistance effect (GMR) sensor (the first process) and then an electric current was sent into wirings for detection connected to both ends of the GMR sensor and into the GMR sensor itself to collect the magnetic particles on the sensor (the second process). In the constitution, however, both the magnetic field caused by the GMR sensor and the magnetic field caused by the wirings connected to the both ends thereof introduce the same magnetic force at the magnetic particles collected in the first process. As a result, the magnetic particles are collected on not only the GMR sensor but also the wirings. The magnetic particles collected on the wirings do not contribute to the detection. The constitution is accordingly not preferable.

SUMMARY OF THE INVENTION

An object of the present invention is to provide a sensor device, a detection method of magnetic particles using the same, and a detection method of a target substance, which can effectively collect the magnetic particles serving as a label on a sensor, and at the same time, reduce the effect given to the sensor by a magnetic field for collecting the magnetic particles.

The sensor device of the present invention is a sensor device for detecting magnetic particles, wherein a detection surface for detecting the magnetic particles is provided, and comprises: a sensor element capable of generating a magnetic field for collecting the magnetic particles on the detection surface by application of a current; a current applying unit for letting flow the current to the sensor element; and a signal taking out unit for obtaining an electrical output signal as a change in the magnetic field on the detection surface.

The current applying unit can have a circuit containing the sensor element, and, in a vessel in which at least magnetic particles can exist, the cross section perpendicular to the current of the sensor element is smaller than the cross section perpendicular to the current of the wiring of the current applying unit capable of generating a magnetic field for collecting the magnetic particles on the detection surface by application of a current and connecting to the magnetic sensor element, and the center axis in the length direction of the sensor element is displaced from the center axis in the length direction of the wiring toward a region in which many of the magnetic particles exist.

Here, a wiring in the sensor element for letting flow the current for generating the magnetic field for collecting the magnetic particles and a wiring in the sensor element for obtaining a change in the magnetic field as an electrical output signal are preferably common at least in part.

Further, as the sensor element, a magnetic impedance effect element can be used. In that case, by applying an alternating current to the sensor element, a change in the magnetic field on the detection surface can be converted into an electrical output signal. Further, for the sensor element, when using the magnetic impedance effect element, the current for generating the magnetic field on the detection surface is a direct current, and when obtaining an output signal, a switch mechanism for changing the current applied to the sensor element into the alternating current is preferably further provided.

On the other hand, as the sensor element, a Hall element and a magneto-resistive element can be also used. As the magneto-resistive element, a spin tunnel magneto-resistive effect element can be used.

In these sensor devices, the current applying unit has a circuit including the sensor element, and inside the circuit, the area of a cross-section vertical to the current of the portion having the detection surface of the sensor element is preferably the smallest.

Further, a magnetizing unit of the magnetic particles is preferably further provided.

Further, the target substance is preferably indirectly detected by detecting the magnetic particles that function as a label of the target substance comprising a non-magnetic substance. In that case, a capturing material for specifically capturing the target substance on the detection surface is provided, and the capturing of the target substance toward the capturing material is preferably detected with the magnetic particles as a label. As the target substance, a biological material can be cited. When an antigen is detected as a biological material, the antibody can be used as the capturing material, and in this case, the sensor device can be used for an immunoassay.

The detection method of the magnetic particles of the present invention is a detection method of the magnetic particles for detecting the magnetic particles in a specimen by using the sensor element capable of generating the magnetic field for collecting the magnetic particles on the detection surface in contact with the specimen by application of the current, and comprises the steps of: applying the current for generating the magnetic field to the sensor element in a state in which the specimen is allowed to contact or come close to the detection surface of the sensor element; and taking out a change in the magnetic filed as an electrical output signal when the magnetic particles gather on the detection surface.

The current applying unit can have a circuit containing the sensor element, and, in a vessel in which at least magnetic particles can exist, the cross section perpendicular to the current of the sensor element is smaller than the cross section perpendicular to the current of the wiring of the current applying unit capable of generating a magnetic field for collecting the magnetic particles on the detection surface by application of a current and connecting to the magnetic sensor element, and the center axis in the length direction of the sensor element is displaced from the center axis in the length direction of the wiring toward a region in which many of the magnetic particles exist.

As the sensor element, a magnetic impedance effect element can be used. In this case, by applying the alternating current to the sensor element, a change in the magnetic field on the detection surface is preferably converted into an electrical output signal. In that case, the current for generating the magnetic field on the detection surface is a direct current, and when the output signal is obtained, a step of changing the current applied to the sensor element in the alternating current is preferably provided.

On the other hand, as the sensor element, a Hall element and a magneto-resistive element can be also used. As the magneto-resistive element, a spin tunnel magneto-resistive effect element can be also used.

Further, a step of magnetizing the magnetic particles is preferably further provided.

Further, by detecting the magnetic particles that function as a label of the target substance comprising a non-magnetic substance, the target substance is preferably indirectly detected. In that case, a capturing material for specifically capturing the target substance on the detection surface is provided, and the capturing of the target substance toward the capturing material is preferably detected with the magnetic particles as a label. As the target substance, a biological material can be cited. When an antigen is detected as a biological material, as the capturing material, the antibody can be used, and in this case, the above described detection method can be used for an immunoassay.

The detection method of the target substance of the present invention is a detection method comprising a capturing material capable of specifically binding to the target substance on the detection surface in contact with the specimen, and moreover, detecting the target substance as a non magnetic substance in the specimen with the magnetic particles as a label by using the sensor element capable of generating a magnetic field for collecting the magnetic particles on the detection surface by application of the current, and comprises the steps of: allowing the specimen to contact the surface of the detection surface of the sensor element; adding the magnetic particles as a label for detecting a conjugate with the capturing material and the target substance to the specimen in contact with the detection surface; generating the magnetic field for collecting the magnetic particles on the detection surface in contact with the specimen in a state in which the magnetic particles are added to the sensor element; and detecting the presence or absence of the formation of the conjugate of the target substance with the capturing material by contact with the specimen on the detection surface of the sensor element by using an electrical output signal based on a change in the magnetic field by taking out the magnetic particles toward the conjugate.

The current applying unit can have a circuit containing the sensor element, and, in a vessel in which at least magnetic particles can exist, the cross section perpendicular to the current of the sensor element is smaller than the cross section perpendicular to the current of the wiring of the current applying unit capable of generating a magnetic field for collecting the magnetic particles on the detection surface by application of a current and connecting to the magnetic sensor element, and the center axis in the length direction of the sensor element is displaced from the center axis in the length direction of the wiring toward a region in which many of the magnetic particles exist.

In the detection method of the target substance also, the preferable mode cited by the above described detection method of the magnetic particles similarly holds true as a preferable mode.

Further features of the present invention will become apparent from the following description of exemplary embodiments with reference to the attached drawings.

DESCRIPTION OF THE EMBODIMENTS

A sensor device of the present invention comprises by including at least a sensor element for magnetic particle detection and a signal taking out unit for taking out an output signal from the sensor element when the sensor element detects the magnetic particles. The sensor element comprises a detection surface (hereinafter, referred to as sensor surface) for performing the detection of magnetic particles, and further, is adapted to generate a magnetic field for collecting the magnetic particles on the sensor surface by application of the current at the measuring time. According to this sensor device, the sensor surface of the sensor element is brought into contact with or put into a close vicinity to a specimen (sample as the detection target) so that the detection of the magnetic particles in the specimen can be performed. Here, "close vicinity" means, for example, the disposition of the specimen within 1 mm of the sensor surface.

The sensor element may be capable of generating a magnetic field for collecting the magnetic particles on the sensor surface by application of the current, and moreover, capable of taking out a change in the magnetic field created by collecting the magnetic particles on the sensor surface as an output signal (change in the voltage and change in the current). Further, when this target substance is indirectly detected by capturing the target substance bonded with the magnetic matter as a label by the capturing material, the sensor element may be such that it can immobilize the capturing material on the sensor surface. As such sensor element, a magnetic impedance effect element, Hall element, magneto-resistive effect element, and the like can be cited.

When the magnetic impedance effect element is used, a change in the magnetic field on the sensor surface can be converted into an electrical output signal (change in the current and voltage) by application of the alternating current. Further, when this magnetic impedance effect element is allowed to generate the magnetic field for attracting the magnetic particles by application of a direct current, or when the output signal is obtained by application of the alternating current, a switch mechanism for changing over these currents is further added to the device.

Figure 8:
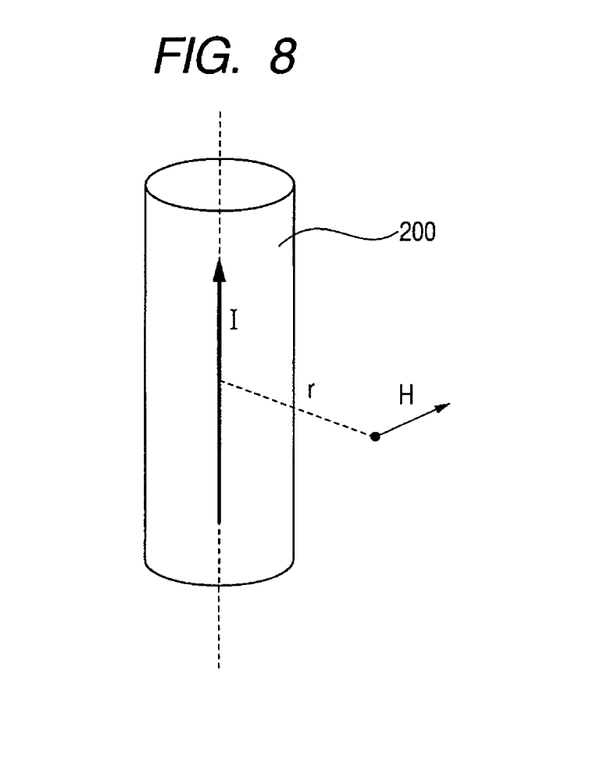
FIG. 8 is a conceptual illustration to describe a magnetic field formed by the magnetic field flowing in the magnetic sensor.

Further, the magnetic impedance effect is reported in CoFeSiB amorphous wire and the like. In such a wire-shaped magnetic impedance effect element, when a circuit is formed by connecting a wiring to this element, a cross-sectional area of the magnetic impedance effect element is preferably made the smallest in the circuit. Here, the "cross-sectional area" means a surface vertical to the direction of the current flowing on the magnetic impedance effect element. The reason why the cross-sectional area is made the smallest is because the largest magnetic field can be allowed to generate in the surface of the magnetic sensor element. That is, by making the cross-sectional area of the magnetic sensor element smaller than a portion other than the element, a current density of the magnetic sensor element can be made higher than the portion other than the element. As a result, the strength of the magnetic field made on the periphery of the element can be made higher, so that the magnetic particles can be collected on the surface of the magnetic sensor element. As illustrated in FIG. 8, when a current I flows into a magnetic sensor (a type of conducting wire) 200, the magnitude H of the magnetic field at a point away r from the center of the conducting wire is represented by a formula (1), and to allow the largest magnetic field to be generated on the surface of the magnetic sensor, the magnetic sensor is required to be made thinner than other conducting portions.

Formula 1

$$H = \frac{I}{2\pi r} \quad (1)$$

Figure 9:
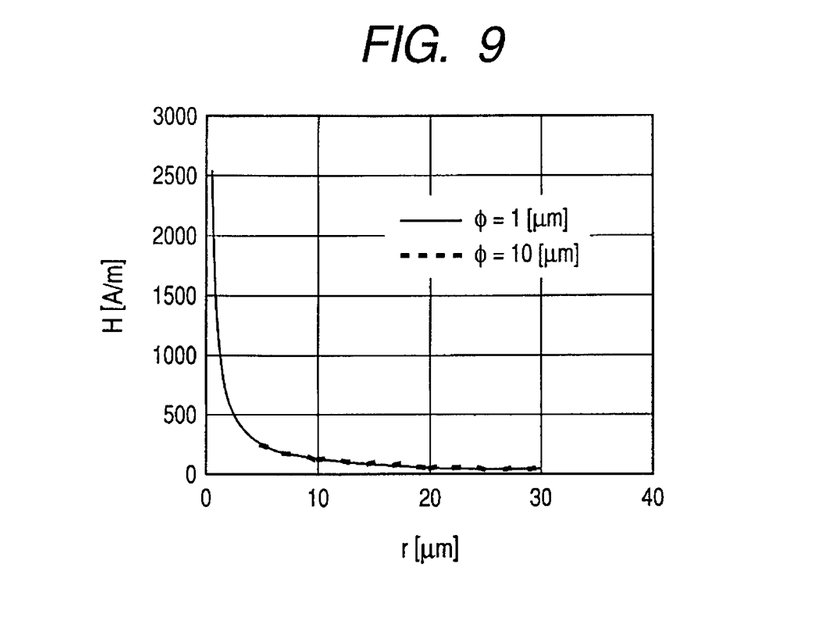
FIG. 9 is a graph illustrating the relation between a distance from the center of conductor and the intensity of magnetic field on the surface of the conductors regarding the device of the present invention.

The following is calculations of magnetic fields caused by 8 mA sent to columnar conductors with infinite length having 1 μm and 10 μm diameters, respectively. As shown in FIG. 9 wherein abscissa r means a distance from the center of conductor and ordinate H means the intensity of magnetic field, the magnetic fields on the surface of the conductors 1 μm and 10 μm in diameter, which are denoted by phi in the figure, are about 2500 A/m and about 250 A/m, respectively. That is, a conductor having a smaller cross section forms a relatively greater magnetic field on the surface thereof.

On the other hand, the magnetic fields at points with a same distance from the center of conductor are the same regardless of a cross section of the conductor. Consequently, it is necessary for collecting efficiently the magnetic particles on the surface of sensor to bring the center of conductor close to the magnetic particles. When there is a maldistribution of current densities in the conductor, it would be necessary to bring the center of distribution of current close to the magnetic particles, of course.

Figure 10:
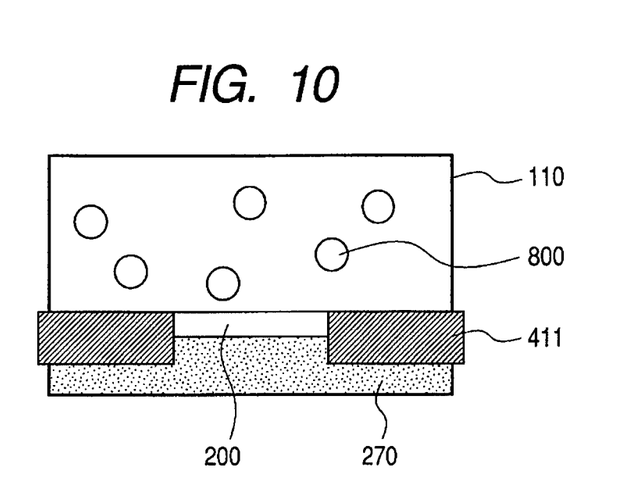
FIG. 10 is a conceptual illustration to describe a configuration of a sensor device of the present invention.

In the aforementioned description, though the magnetic sensor was taken as a columnar shape, in other shapes also such as a rectangular column, similarly the cross-sectional area is preferably smaller than other conducting portions. It is also preferable to bring the center close the magnetic particles. FIG. 10 exemplifies a constitution of such a device. In the figure, the sensor element is located at the bottom of vessel 110 in which the magnetic particles 800 exist, the conductor portion of the sensor element is thinner than the wiring, the sensor element is smaller than the wiring 411 in cross section, and the surface of conductor levels with the surface of wiring. With respect to magnetic particles on the same level, since a greater magnetic force is applied to magnetic particles above the sensor than those above the wiring, the magnetic particles are collected on the surface of sensor with a higher density.

On the other hand, when the magneto-resistive effect element is used as the sensor element, such element has preferably a spin tunnel magneto-resistive effect film (spin tunnel magneto-resistive effect element).

On the other hand, if the magnetic particles have magnetism by magnetizing process, the sensor device can be provided by further adding the magnetizing unit. As the magnetizing unit, an electromagnet can be suitably used.

The magnetic particles may be detected by the magnetic sensor, and from this viewpoint, though the particle size is not limited to a significant restriction, general magnetic particles used for B/F separation (separation of the binding type and free type of antigen-antibody) and the like can be used, and such magnetic particles are available in various particle sizes from several ten μm to several ten nm.

By fixating the capturing material specifically reacting with the target substance on the sensor surface of the sensor element, the target substance in the specimen is captured by this capturing material so as to form a conjugate with the capturing material and target substance, and the formation of this conjugate can be indirectly detected with the magnetic particles as a label. Incidentally, the magnetic particles may be directly and covalently bonded to the target substance, and the capturing material provided in the magnetic particles may capture the target substance.

The capturing material can be selected according to a type of target substance. For example, when one of combination of a specific binding pair is the target substance, the one of combination can be used as the capturing material. As such a combination, antigen/antibody, complementary DNA pair, receptor/ligand, and enzyme/substrate can be cited. Further, as the target substance, a biological material (protein, nucleic acid, sugar chain, lipid, and the like), allergen, bacteria, virus, and the like can be cited. The antigen is used as the capturing material, and can be made as a sensor device for the immunoassay by the sensor element that detects the antigen by the antigen-antibody reaction.

By using the sensor device defined as described above and performing at least the following steps, the detection of the magnetic particles in the specimen can be performed. In this case, the specimen includes the magnetic particles as the detection target in various solvents such as liquid.

(1) A step of applying the current for generating the magnetic field to the sensor element in a state in which the specimen is brought into contact with or put into a close vicinity to the detection surface of the sensor element.

(2) A step of taking out a change in the magnetic field where the magnetic particles are gathered on the detection surface as an electrical output signal.

Further, when the capturing material is immobilized on the sensor surface so as to perform the detection of the target substance, a method comprising the following steps can be suitably utilized.

(1) A step of allowing the specimen to be brought into contact with the detection surface of the sensor element.

(2) A step of adding the magnetic particles as a label for detecting the conjugate with the capturing material and the target substance to the specimen in contact with the detection surface.

(3) A step of allowing the sensor element to generate a magnetic field for collecting the magnetic particles on the detection surface in contact with the specimen in a state added with the magnetic particles.

(4) A step of detecting the presence or absence of the formation of the conjugate with the capturing material and the target substance by contact with the specimen on the detection surface of the sensor element by using an electrical output signal based on a change in the magnetic field through the taking out of the magnetic particles into the conjugate.

The specimen in the detection method of this method is a liquid sample (for example, an aqueous solution of the target substance) as a target of the detection of the presence or absence of the target substance or a target of the measurement of its content and concentration. Further, this specimen, according to need, may be a specimen subjected to preprocesses such as an extraction process, refinery process, and dilution process which are performed in qualitative and quantitative analysis by a sandwich immunoassay and the like. Further, a step can be performed in which the sensor surface and the specimen are brought into contact with each other and are reacted, and after that, according to need, the sensor surface is cleansed, and then, a measurement liquid (buffer solution and the like) is provided or filled in the measurement area, thereby generating a magnetic field for collecting the magnetic particles on the sensor surface. Further, an operation may be performed, in which the magnetic particles as a label are bonded with the conjugate with the capturing material and the target substance, and then, the sensor surface is cleansed, and unreacted magnetic particles are removed from the measurement area, and after that, an output signal for detection is obtained.

The sensor device of the present invention is adapted to generate a magnetic field for collecting the magnetic particles by the current let flow into the sensor, and since the magnetic field to be generated is greater in the vicinity of the sensor element than of the wiring, the magnetic particles can be effectively collected on the sensor surface. Further, according to the configuration of the sensor device of the present invention, since the magnetic field applied on the sensor element is small, the influence to the sensor element by the magnetic field can be reduced.

With the immunoassay device in which the sensor device is a magnetic impedance effect element as an example, the detail of the sensor device of the present invention will be described below in detail.

Figure 1:
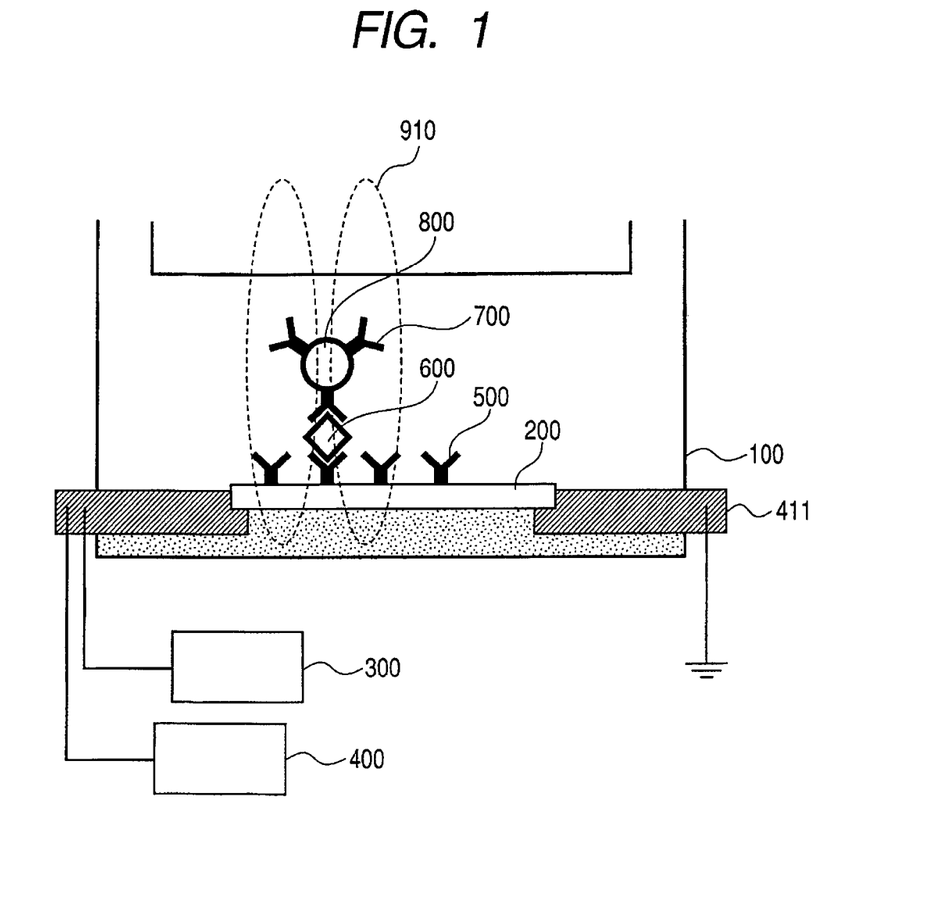
FIG. 1 is a conceptual illustration to describe a configuration of a sensor of the present invention.

As illustrated in FIG. 1, a magnetic sensor 200 as a sensor element is formed in a housing 100, and the magnetic sensor 200 is connected to a detecting circuit 300 and a magnetic field generating circuit 400. Although the magnetic sensor 200 may be any of magnetic field detecting elements such as a magneto-resistive effect element and Hall element, in the present description, it is taken as a wire-shaped magnetic impedance effect element. Magnetic sensor 200 is fixed on the bottom of body 100. Wiring 411 connecting to magnetic sensor 200 has a rectangular parallelepiped shape thicker than the diameter of the magnetic sensor and the same width as the diameter of the sensor. The top of magnetic sensor 200 is on a higher level than the top surface of wiring. On the surface of the magnetic sensor 200, a primary antibody 500 to which an antigen 600 being a target substance specifically binds is immobilized according to the rule.

A specimen solution is injected into the immunoassay device defined as described above. When the specimen solution contains the antigen 600, the antigen 600 binds to the primary antibody 500. Next, while letting flow the current into the magnetic sensor 200, a secondary antibody (antibody binding to the region to which primary antibody of the antigen 600 does not bind) 700 injects the magnetic particles 800 immobilized on the surface according to the rule into the specimen solution inside the housing 100. By the magnetic field created by the current let flow into the magnetic sensor 200, the magnetic particles 800 are attracted by the magnetic sensor 200, so that the antigen 600 and the secondary antibody 700 can be sufficiently reacted without injecting an excessive amount of magnetic particles. The current let flow when collecting the magnetic particles is preferably at the highest density in the magnetic sensor 200. By so doing, the largest magnetic field can be generated in the vicinity of the magnetic sensor 200, and similarly to the configuration disclosed in Document 1, the magnetic particles gathering on the wiring which is not the detection area can be decreased. Further, a magnitude of the magnetic field generated inside the magnetic sensor by the current flowing in the magnetic sensor can be presumed from the following formula (2) which represents the magnitude of a magnetic field H at a point away r from the center of the magnetic sensor.

Formula 2

$$H = \frac{Ir}{2\pi R^2} \quad (2)$$

In the above described formula 2, R indicates a radius of a columned magnetic sensor, and I indicates a current flowing in the magnetic sensor.

In the configuration disclosed in Document 1, the magnetic field applied on the surface of the magnetic sensor is applied approximately on the entire magnetic sensor, and rather than this configuration, the configuration according to the present invention has a relatively weak magnetic field applied on the magnetic sensor 200, so that the magnetic sensor 200 is hard to be affected by the magnetic field.

The magnetic particles 800 are reacted on the surface of the magnetic sensor 200, and after that, when there are the magnetic particles 800 not immobilized on the antigen, these particles are removed. A removing method may be washout or the particles may be alienated from the magnetic sensor 200 by the magnetic field. If the antigen 600 does not exist in the specimen solution, the magnetic particles 800 are not left on the surface of the magnetic sensor 200, and if the antigen 600 exists, in proportion to the number of the antigens, the magnetic particles 800 are immobilized on the surface of the magnetic sensor 200.

As described above, an alternating current is let flow in the magnetic sensor 200 immobilized with the magnetic particles 800, and a stray magnetic field 910 generated from the magnetic particles 800 is detected. Since the detection signals of the magnetic sensor depend on the number of magnetic particles 800, the concentration and the presence or absence of the antigen can be indirectly known by the magnitude of the detection signal.

When the magnetic particles 800 illustrate superparamagnetism, in case it is detected, the magnetic field is applied from the outside so as to generate any magnitude of magnetization.

The magnetic field for collecting the magnetic particles 800 may use one of the DC current and the AC current. Further, by using the AC power source used at the measuring time, the current for generating the magnetic field may be let flow.

For the antibody used in the present invention, the one used conventionally can be used. Further, for the secondary antibody immobilized to the magnetic particles, similarly, various types of antibodies can be used. As a specimen, the antibody such as a biological material (protein, nucleic acid, and sugar chain), allergen, bacteria, and virus, which can be specifically recognized and is non-magnetic substance, becomes the target. Further, the present invention can detect whatever material it is, if the material can detect not only the biomolecule, but also directly or indirectly immobilize the magnetic particles.

EXAMPLES

The present invention will be described further in detail below by citing examples.

Example 1

In the present example, an example of the production method of a magnetic sensor of the present invention will be described.

Wiring 411 is embedded in a bottom of glass tube 100. A rectangular parallelepiped magnetic sensor 200 comprising a CoFeSiB amorphous is fixed above the wiring. The width is the same as a half of the width in the magnetic sensor. The upper surface of wiring 411 levels with the height of the bottom of glass tube. The wiring 411 is connected to a DC power source 410 and an AC power Source 320 through a selector switch 310. The wiring 411 has a thickness three times as greater and the same width as the width of magnetic sensor 200. The AC power source is connected to a fixed resister 330 in series with the magnetic sensor 200. Further, the fixed resister 330 is connected to a voltmeter 340 (see FIG. 2).

In the present example, while a rectangular parallelepiped magnetic impedance effect element is used, it may be a wire-shaped or thin film-shaped element or may be a magnetic impedance effect element having a sandwich structure of the magnetic film of a magnetic film/metal film/magnetic film capable of realizing thinning much more of the film. Further, it may be a magnetic impedance effect film having a structure winding the periphery of the metal film by the magnetic film, which effect film can be made thin much more.

Figure 2:
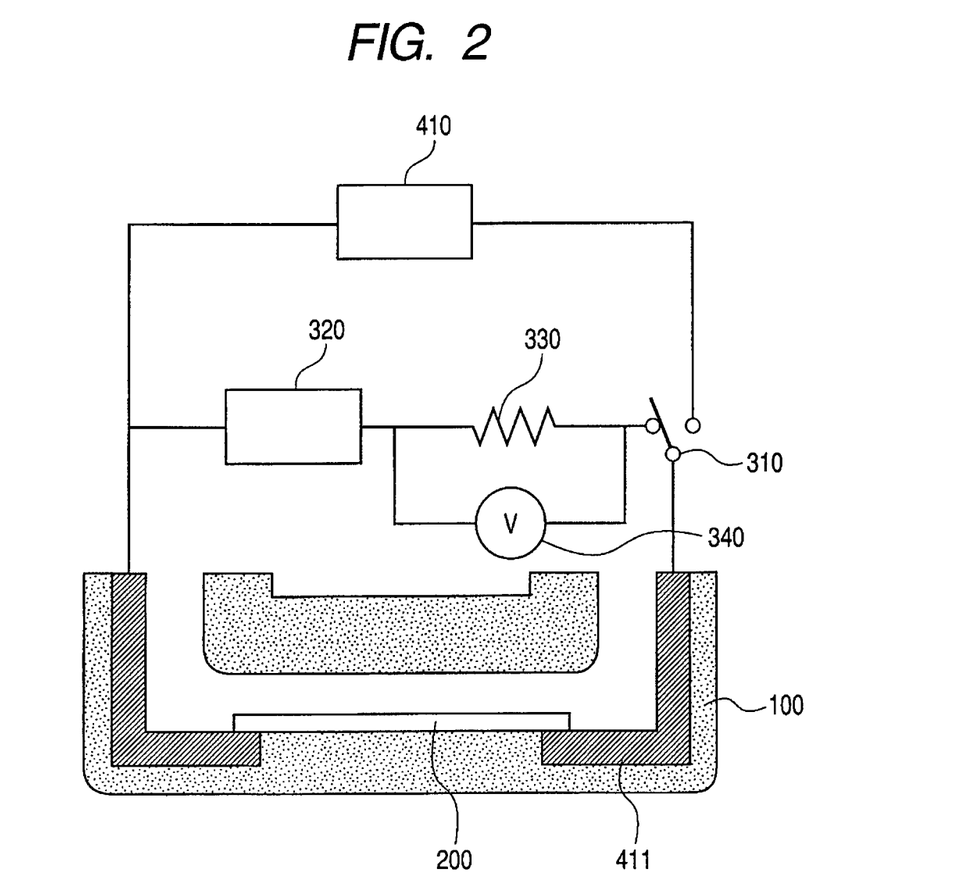
FIG. 2 is a conceptual illustration to describe a first embodiment of the sensor of the present invention.

On the surface of the magnetic sensor 200, a $SiO_2$ film being an insulating film is formed, and further, an Au film is formed so as to be immobilized with the primary antibody 500. In the present example, the primary antibody 500 and the secondary antibody 700 use a substance specifically binding to a prostate-specific antigen (PSA) which is the target substance 600.

First, a detection current of 10 MHz is let flow by the AC power source 320, and an initial impedance value is measured. Next, a blood which is a specimen solution is injected into the glass tube, and is incubated. After the incubation, the selector switch 310 is switched over, and the DC current is let flow in the magnetic sensor 200 by the DC power source 410 so as to form the magnetic field, and at the same time, the magnetic particles 800 immobilized with the secondary antibody 700 on the surface are injected into the glass tube 100. The magnetic particles to be used comprise $Fe_3O_4$, and a total particle size including the antibody is approximately 4.5 µm. The injected magnetic particles 800 are gathered on the surface of the magnetic sensor 200 by the magnetic field generated from the magnetic sensor 200. The magnetic field generated at the surface of the wiring, which is connected to both ends of the magnetic sensor 200, is relatively weak since the cross-sectional area of the wiring is narrow. Consequently, the magnetic particles 800 are prone to gather on the surface of the magnetic sensor 200. By collecting the magnetic particles 800 on the surface of the magnetic sensor 200, the concentration of the magnetic particles 800 can be made thinner than the conventional concentration, and at the same time, the reaction time can be made shorter. After the magnetic particles 800 are immobilized on the target substance, the flow of DC current is halted, and the magnetic particles 800 not immobilized by phosphoric acid buffer solution are removed. After that, the selector switch 310 is switched over, and the AC current is let flow again so as to measure the impedance value. By checking a variation in the impedance value and initial value, the amount of the immobilized magnetic particles 800, that is, the concentration of the PSA of the specimen solution can be known.

Example 2

In the first example, while the magnetic impedance effect element is used as the magnetic sensor 200, even a Hall element can detect the magnetic particles 800 by the same configuration. Since a detection signal is hard to saturate even if a Hall element has a large magnetic field, a method for applying a sufficiently large DC magnetic field to the magnetic particles 800 so as to magnify the magnetization of the magnetic particles 800, thereby magnifying the stray magnetic field generated from the magnetic particles 800 is suited to the Hall element.

Figure 3:
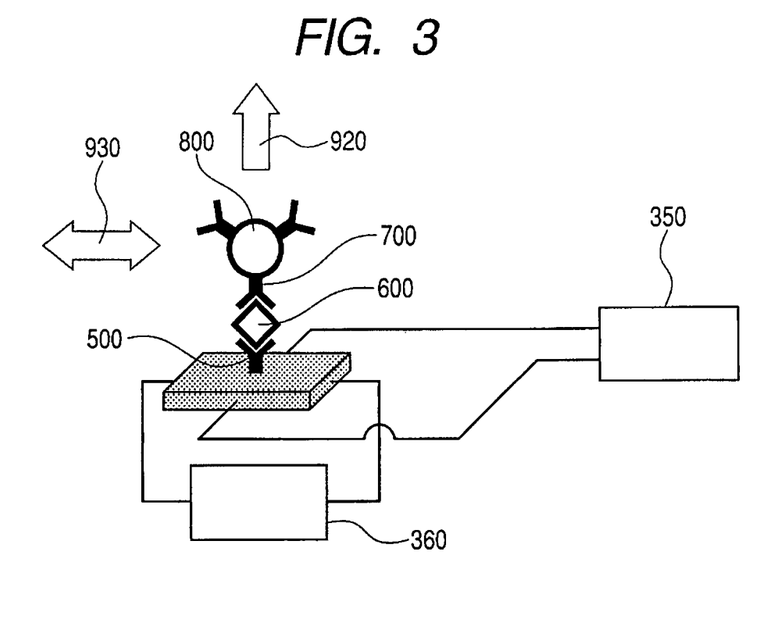
FIG. 3 is a conceptual illustration to describe a first embodiment of the sensor of the present invention.

In the Hall element, since the detection signal is generated in the direction vertical to the current which is let flow into the element, the connection between the power sources and the detection circuit is performed as illustrated in FIG. 3. As the detection current, a DC power source 360 is used. To separate the detection signal and noise, a lock-in amplifier 350 is used. Further, to steer the magnetization direction of the magnetic particles in the direction vertical to the surface of the Hall element, the magnetic field 930 is applied in the direction vertical to the element surface, and furthermore, an AC magnetic field 920 of a desired frequency is applied in the direction of the inner surface of the element so as to change the magnetizing direction of the magnetic particles. By so doing, the magnitude of the effective magnetic field applied on the Hall element is changed, thereby obtaining a detection signal component of the frequency.

Figure 5:
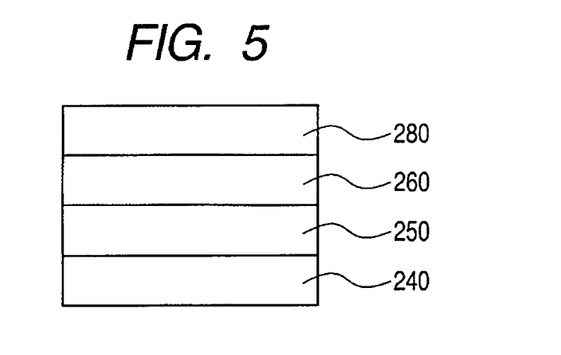
FIG. 5 is a cross-sectional view to describe a film configuration of a Hall element used in the present invention.

As the Hall element, in the present example, as illustrated in FIG. 5, the one forming an InSb film 250 on a GaAs substrate 240 is used. A $SiO_2$ film 260 is formed on the InSb film 250 as an insulating film, and further, on that film, an Au film 280 is formed, and on this surface, a primary antibody 500 is immobilized.

The fixation of the target substance 600 and the magnetic particles 800 is performed similarly to the first example.

Example 3

Further, a magneto-resistive effect element can be used for a magnetic sensor 200. The magneto-resistive effect element is used as the detection device of a magnetic disk, and is suited to a configuration for detecting a micro magnetic field generated from a micro region.

A detection current uses a DC power source 360, and the detection current is let flow so as to pass through a spin tunnel film 230 between an upper magnetic substance film 210 and the lower magnetic substance film 220. When a spin tunnel magneto-resistive (TMR) effect film is used for a magneto-resistive effect film, an attention must be paid so that an upper magnetic substance film 210 and a lower magnetic substance film 220 are not short-circuited (see FIG. 4).

Figure 4:
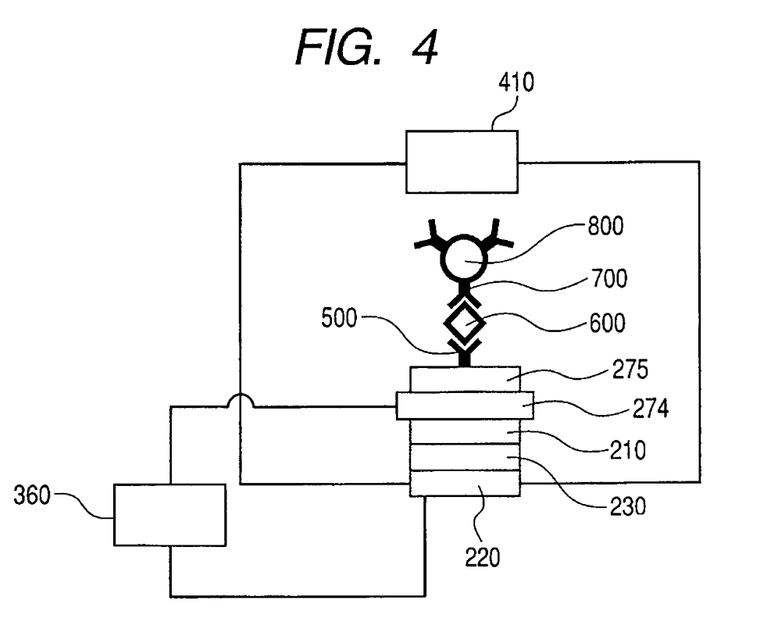
FIG. 4 is a conceptual illustration to describe a first embodiment of the sensor of the present invention.

In FIG. 4, while the current is let flow into the lower magnetic substance film 220, the current may be let flow into the upper magnetic substance film 210 or after being disposed so as not to be short-circuited, both of the magnetic substance films may be given the current. However, the center level in the direction of thickness of the wiring for sending a current in magnetic films 220 and/or 210 is below that of each magnetic film, and the cross sections of the wirings are greater than the cross sections of magnetic films.

Figure 6:
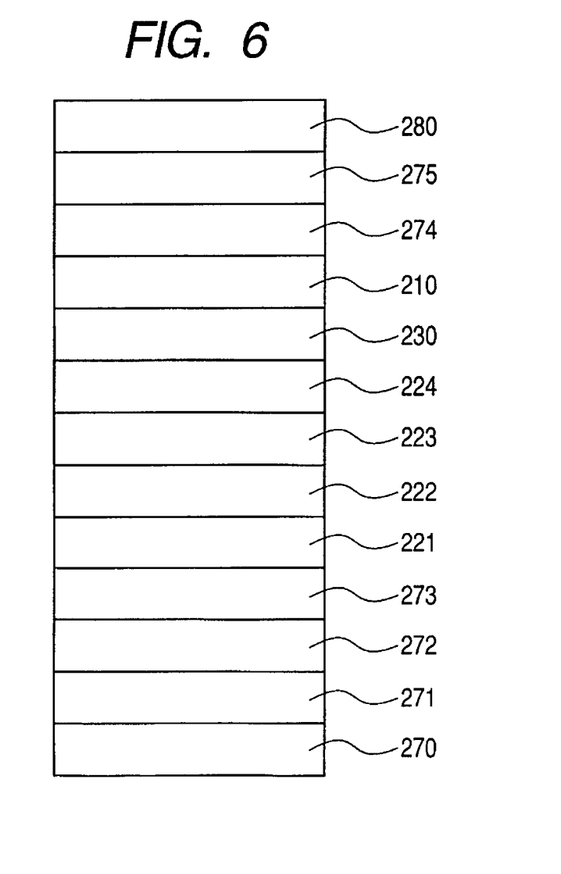
FIG. 6 is a cross-sectional view to describe a film configuration of a magneto-resistive effect element used in the present invention.

As the magneto-resistive effect element, in the present example, as illustrated in FIG. 6, a multilayer film of a Ta film 271, Cu film 272, and Ta film 273 on a Si substrate 270 as a ground film, a multilayer film of a PtMn film 221, CoFe film 222, Ru film 223, and CoFeB film 224 as a lower magnetic substance film 220, and a multilayer film forming in order a MgO film as a spin tunnel film 230 and a CoFeB film as an upper portion magnetic substance film 210 are used. On the upper portion of the magnetic substance film 210, a Pt film 274 as a protection film and an upper wiring 275 for letting flow detection current are disposed. On the sensor surface, an Au film 280 is formed, and a primary antibody 500 is immobilized.

When the magnetization of the magnetic particles does not reach saturation and the detection signal is small, the magnetic particles are applied with the magnetic field from the outside so as to magnify the magnetization, thereby enabling the detection signal to become large.

By using the sensor device according to the exemplary embodiment of the present invention, the magnetic particles serving as a label can be effectively collected on the sensor, and at the same time, the influence given to the sensor by the magnetic field for collecting the magnetic particles can be reduced.

Further, by using the sensor and the sensing method according to the exemplary embodiment of the present invention, an immunoassay can be performed with relatively fewer magnetic particles and within a short period of time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-100560, filed Mar. 31, 2006, which is hereby incorporated by reference herein in its entirety.

What is claimed is:

1. A sensor device for detecting magnetic particles in a specimen, comprising:
    a sensor element having a detection surface for detecting the magnetic particles and capable of generating a magnetic field for collecting the magnetic particles on the detection surface by application of a current;
    a current applying unit for letting the current flow to the sensor element; and
    a signal taking out unit for obtaining a change in the magnetic field on the detection surface as an electrical output signal,
    wherein a circuit is formed by connecting the current applying unit to the sensor element with a wiring,
    wherein a cross-sectional area of the sensor element perpendicular to a direction of the current flowing on the sensor element is smaller than a cross-sectional area of the wiring perpendicular to a direction of the current flowing on the wiring, and
    wherein the center axis in the length direction of the sensor element is displaced from the center axis in the length direction of the wiring toward a region of the sensor device in which the magnetic particles exist.

2. The sensor device according to claim 1, wherein a wiring in the sensor element for letting a current for generating the magnetic field flow and a wiring in the sensor element for obtaining a change in the magnetic field as an electrical output signal are common at least in part.

3. The sensor device according to claim 1, wherein a target substance comprising a non-magnetic substance is indirectly detected by detecting the magnetic particles such that the magnetic particles function as a label of the target substance.

4. The sensor device according to claim 1, wherein the sensor element extends from one portion of the wiring to another portion of the wiring.

5. The sensor device according to claim 1, wherein the top of the sensor element is on a higher level than the top surface of the wiring.

* * * * *